US012013329B1

(12) United States Patent
Haruta

(10) Patent No.: US 12,013,329 B1
(45) Date of Patent: Jun. 18, 2024

(54) DETECTION APPARATUS

(71) Applicant: P&M Co., Ltd., Fukushima (JP)

(72) Inventor: Mineyuki Haruta, Fukushima (JP)

(73) Assignee: P&M Co., Ltd., Fukushima (JP)

( * ) Notice: Subject to any disclaimer, the term of this patent is extended or adjusted under 35 U.S.C. 154(b) by 0 days.

(21) Appl. No.: 17/799,875

(22) PCT Filed: Mar. 11, 2022

(86) PCT No.: PCT/JP2022/011101
§ 371 (c)(1),
(2) Date: Aug. 15, 2022

(87) PCT Pub. No.: WO2022/196587
PCT Pub. Date: Sep. 22, 2022

(30) Foreign Application Priority Data

Mar. 15, 2021 (JP) .................. 2021-041469

(51) Int. Cl.
*G01N 15/1434* (2024.01)
*A61M 5/168* (2006.01)

(52) U.S. Cl.
CPC ....... *G01N 15/1434* (2013.01); *A61M 5/1689* (2013.01)

(58) Field of Classification Search
CPC .................. G01N 15/1434; A61M 5/1689
See application file for complete search history.

(56) References Cited

U.S. PATENT DOCUMENTS

| 4,533,350 | A | 8/1985 | Danby et al. | |
|---|---|---|---|---|
| 8,730,479 | B2 * | 5/2014 | Ness ................. | G01N 21/6428 356/441 |
| 11,419,982 | B2 * | 8/2022 | Hirata ................ | A61M 5/1689 |

FOREIGN PATENT DOCUMENTS

| CN | 2659458 Y | 12/2004 |
|---|---|---|
| CN | 101856525 B | 3/2012 |
| JP | S6476871 A | 9/1987 |
| JP | 2014204897 A | 10/2014 |
| JP | 2015152394 A | 8/2015 |

(Continued)

OTHER PUBLICATIONS

Japanese Office Action corresponding with Japanese Application No. 2021-041469 dated Aug. 23, 2021 with Machine English Translation.

(Continued)

*Primary Examiner* — Seung C Sohn
(74) *Attorney, Agent, or Firm* — Renner, Otto, Boisselle & Sklar, LLP

(57) ABSTRACT

The problem to be solved of the present disclosure is to provide a detection apparatus that detects dropping of a droplet. The detection apparatus comprises an optical element array having three or more optical elements comprising a first light emitting element, a first light receiving element and a second light receiving element, wherein the first light emitting element, the first light receiving element and the second light receiving element are disposed within the optical element array so that a part of a light emitting region irradiated from the first light emitting element and a part of a light receiving region of the first light receiving element overlap and a part of a light emitting region irradiated from the first light emitting element and a part of a light receiving region of the second light receiving element overlap.

8 Claims, 7 Drawing Sheets

(56) References Cited

FOREIGN PATENT DOCUMENTS

JP       2017202259 A    11/2017
KR    2020-0020075 A     2/2020

OTHER PUBLICATIONS

International Search Report corresponding with Application No. PCT/JP2022/011101 mailed Apr. 5, 2022.
Extended European Search Report (EESR), including the supplementary European search report and the European search opinion for European Application No. 22750654.0 dated Feb. 5, 2024.

* cited by examiner

[Figure 1]
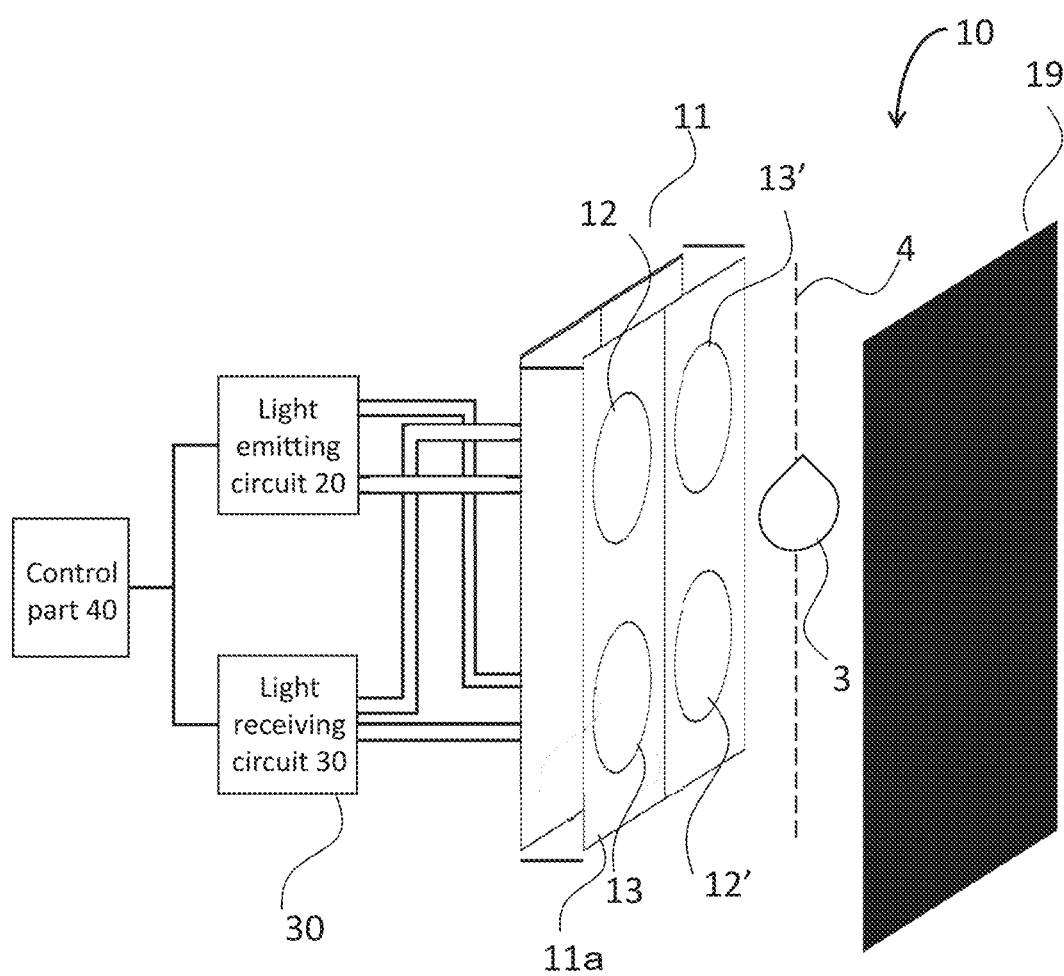

[Figure 2]
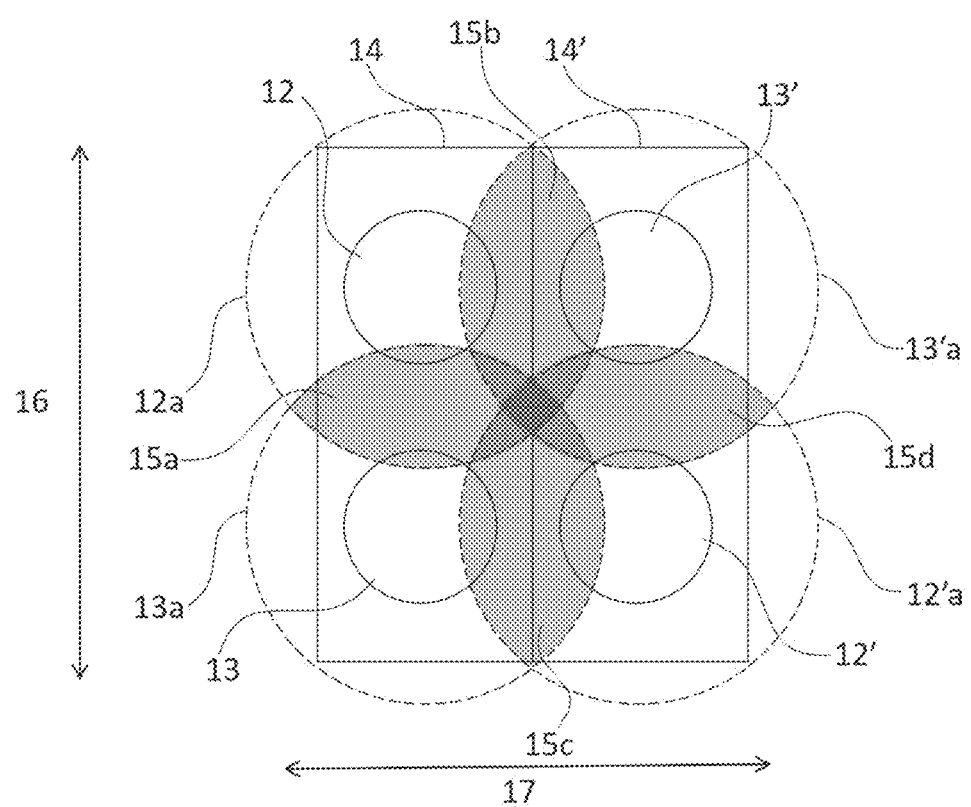

[Figure 3]
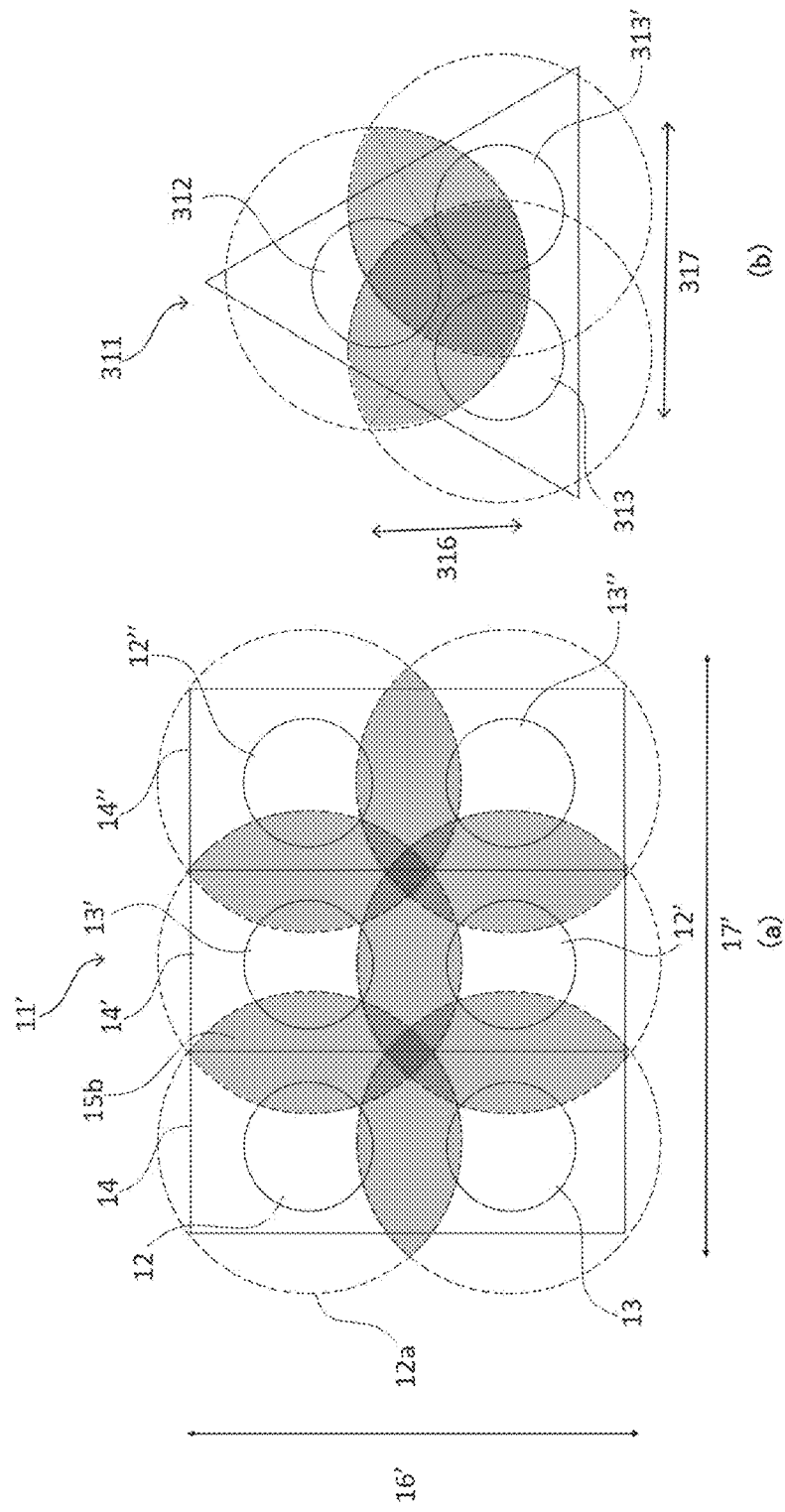

[Figure 4]
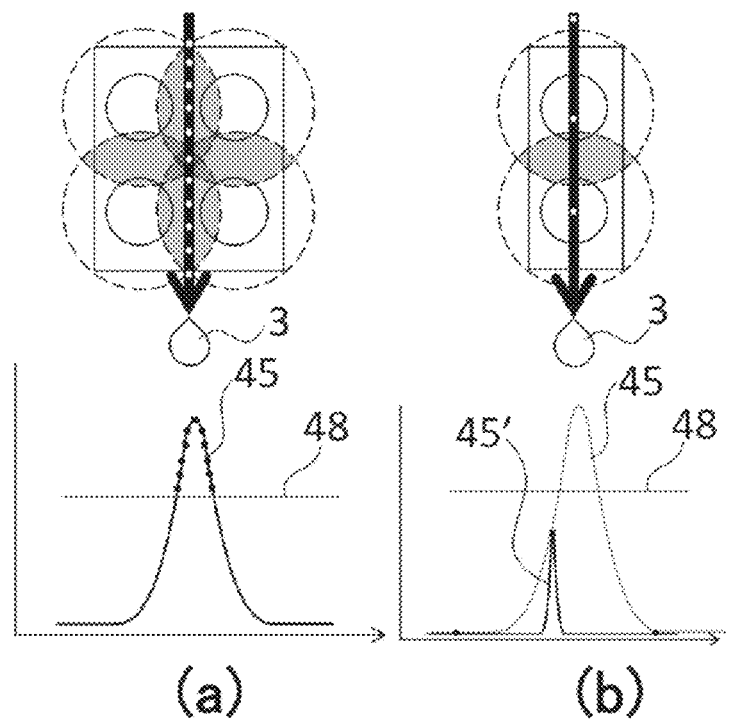
[Figure 5]
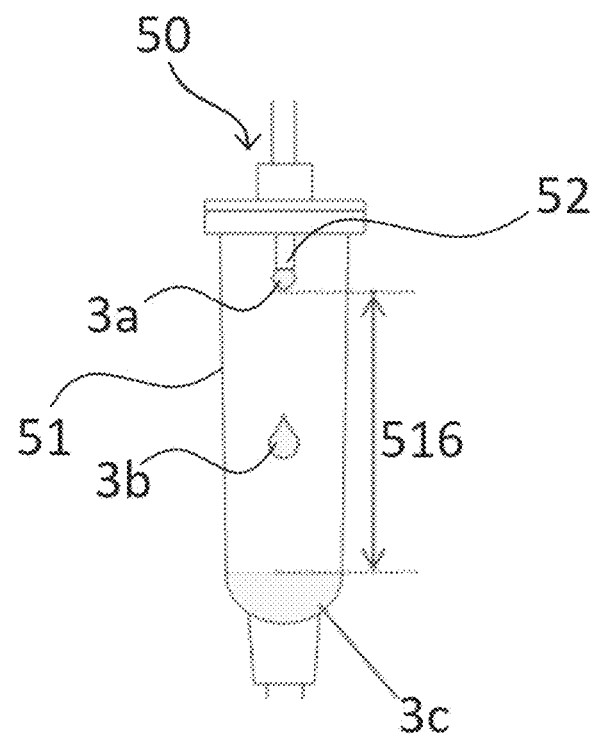

[Figure 6]
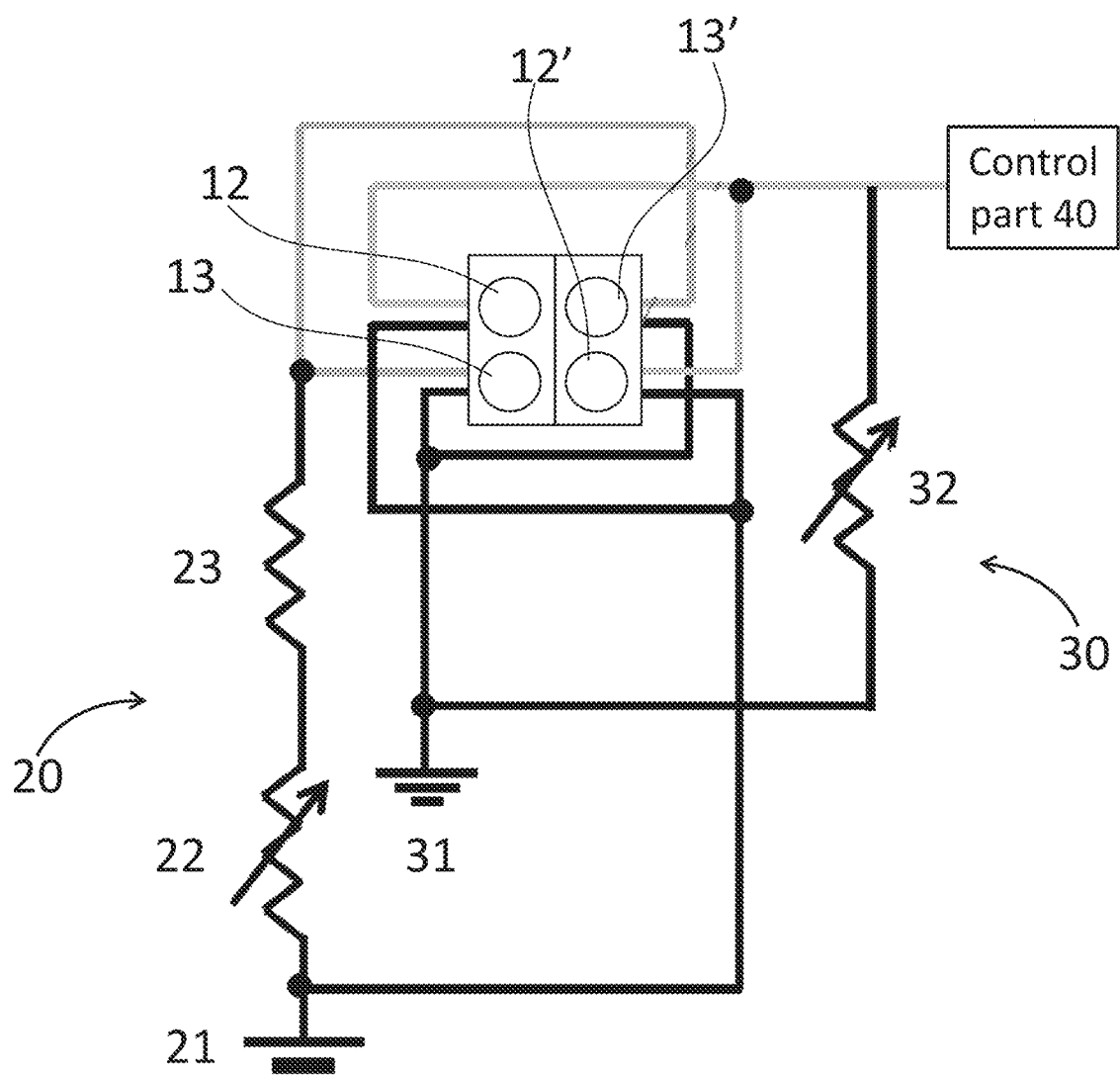

[Figure 7]
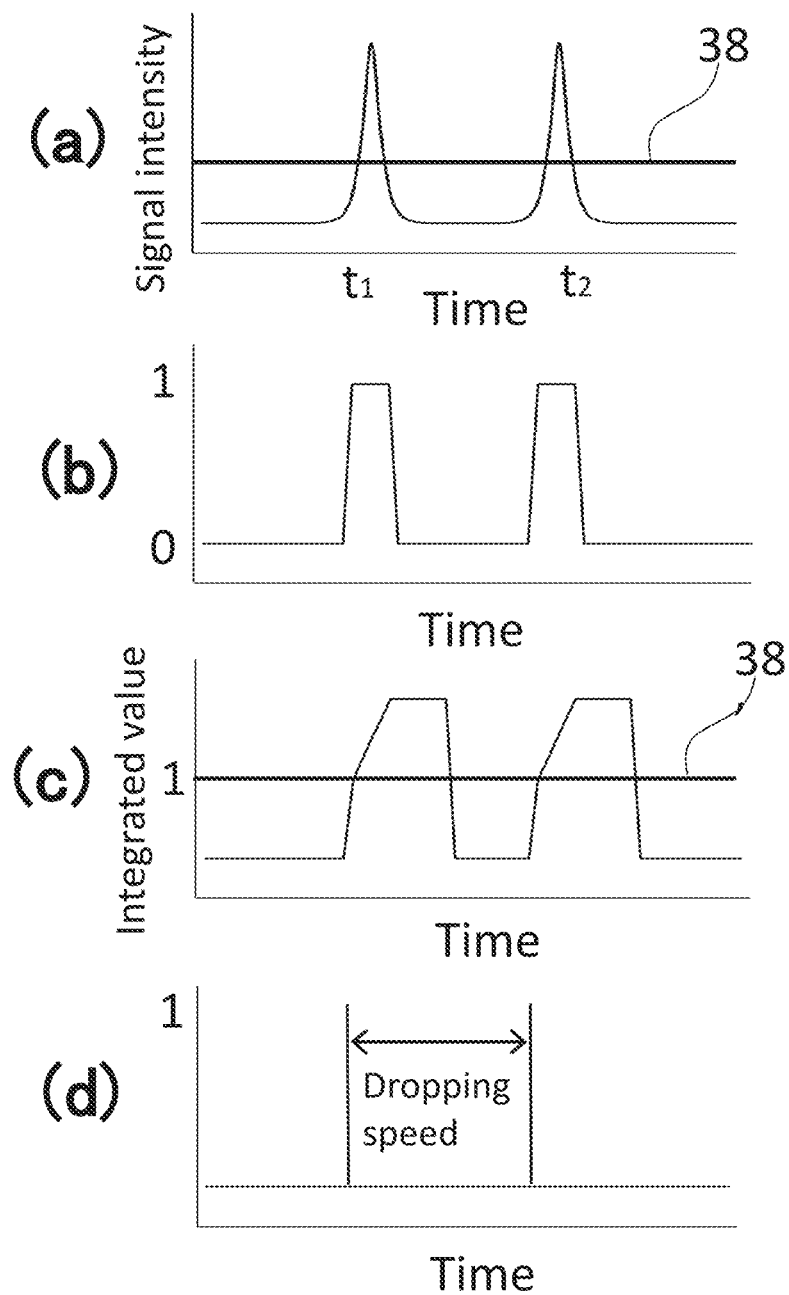

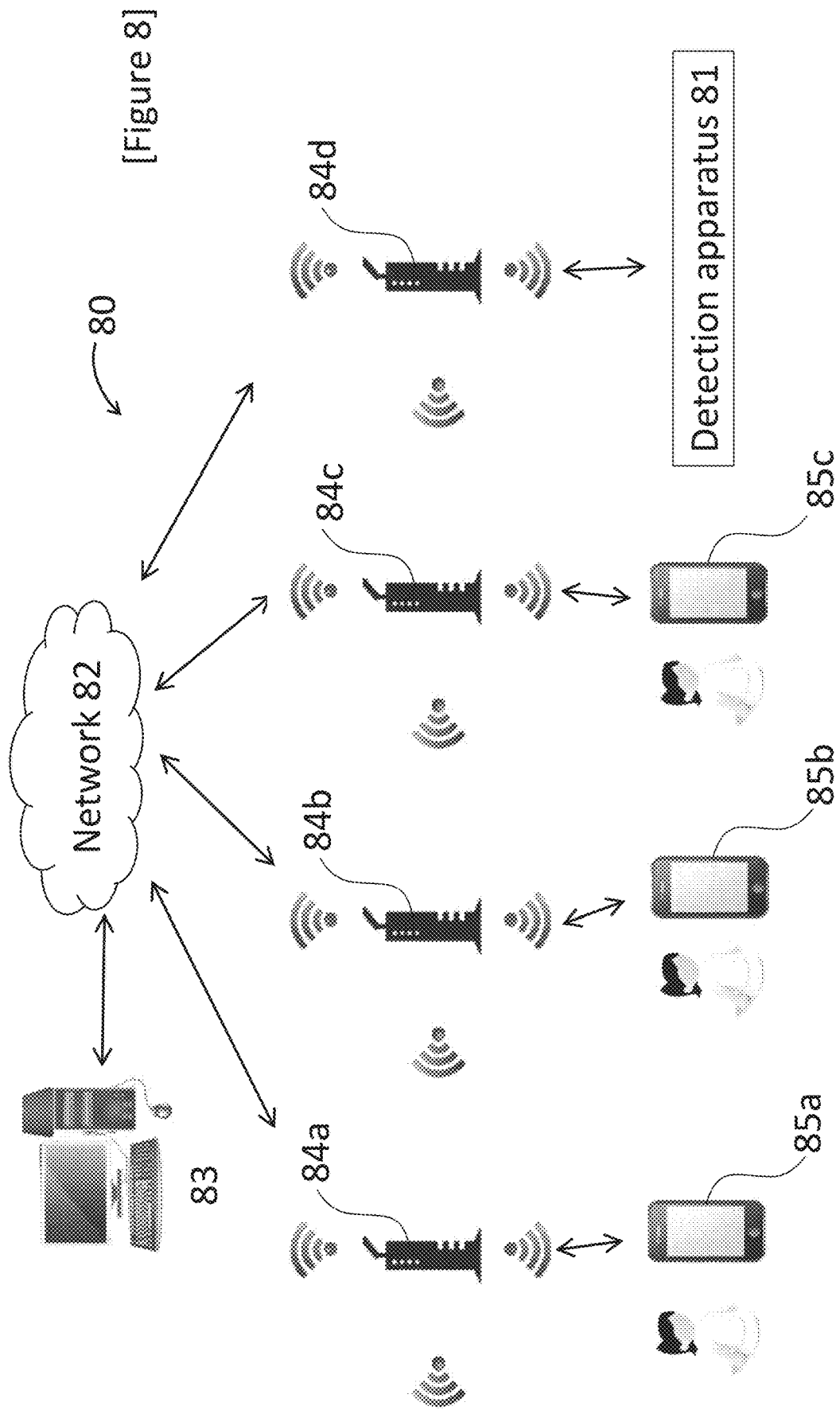

DETECTION APPARATUS

This application is a national phase of International Application No. PCT/JP2022/011101 filed 11 Mar. 2022, which claims priority to Japan Application No. 2021-041469 filed 15 Mar. 2021, the entireties of which are hereby incorporated by reference.

TECHNICAL FIELD

The present disclosure is generally directed to a detection apparatus that detects dropping of a droplet, especially directed to a detection apparatus that detects dropping of drip infusion of an agent used in the medical field.

BACKGROUND ART

Conventionally, a drip infusion monitoring apparatus that detects dropping of drip infusion using a light emitting element and a light receiving element is known.

Patent Literature 1 discloses an infusion pump with the function of detecting dropping of drip infusion. This infusion pump comprises a dropping detector, wherein the dropping detector disposes one light emitting element and one light receiving element opposite to a drip infusion passing position to utilize the change in the amount of light entering the light receiving element by refraction and shading of light when the light irradiated from the light emitting element passes drip infusion to detect dropping based on the change in the voltage of the light receiving element.

CITATION LIST

Patent Literature

[PTL 1] Japanese Laid-Open Publication No. 2014-204897

SUMMARY OF INVENTION

Technical Problem

The object of the present disclosure is to provide a new detection apparatus that can improve the ability to detect dropping of a droplet and a droplet information notification system utilizing the detection apparatus.

Solution to Problem

The inventors of the present invention developed a droplet detection apparatus that can improve the detection ability by efficiently expanding the detection range of the dropping of a droplet as a result of earnest study. In one aspect, the droplet detection apparatus of the present disclosure comprises an optical element array having three or more optical elements and a reflection prevention member that prevents reflection of light from the optical element array to a light receiving element. In one aspect, the droplet information notification system of the present disclosure comprises a detection apparatus that obtains droplet information, a network wherein the droplet information is communicated and one or more terminal that receives the droplet information.

Therefore, the present disclosure provides the following items.

(Item 1)
A detection apparatus that detects dropping of a droplet, wherein the detection apparatus comprises:
an optical element array having three or more optical elements comprising a first light emitting element, a first light receiving element and a second light receiving element,
wherein the first light emitting element, the first light receiving element and the second light receiving element are disposed within the optical element array so that:
a part of a light emitting region irradiated from the first light emitting element and a part of a light receiving region of the first light receiving element overlap; and
a part of a light emitting region irradiated from the first light emitting element and a part of a light receiving region of the second light receiving element overlap.

(Item 2)
The detection apparatus of item 1, wherein the three or more optical elements further comprise a second light emitting element,
wherein the first light emitting element, the first light receiving element, the first light receiving element and a second light emitting element are disposed within the optical element array so that:
a part of a light emitting region irradiated from the second light emitting element and a part of a light receiving region of the first light receiving element overlap; and
a part of a light emitting region irradiated from the second light emitting element and a part of a light receiving region of the second light receiving element overlap.

(Item 3)
The detection apparatus of item 2,
wherein the first light emitting element and the second light receiving element are disposed on the upstream side of a pathway where the droplet passes, and
wherein the second light emitting element and the first light receiving element are disposed on the downstream side of a pathway where the droplet passes.

(Item 4)
The detection apparatus of item 2 or 3, wherein the optical element array comprises:
a first optical element subarray comprising a first light emitting element and a first light receiving element; and
a second optical element subarray comprising a second light emitting element and a second light receiving element,
wherein the first optical element array and the second optical element array are disposed adjacent to one another.

(Item 5)
The detection apparatus of item 4, wherein the second optical element subarray is configured to be detachable with respect to the first optical element subarray.

(Item 6)
The detection apparatus of any one of items 1 to 5, comprising a reflection prevention member disposed on the other side of a side where the optical element array is disposed with respect to a pathway where the droplet passes.

(Item 7)
The detection apparatus of item 5, wherein the reflection prevention member comprises a black color region.

(Item 8)
The detection apparatus of anyone of items 1 to 7, wherein a light emitting wavelength of the first light emitting element and a light receiving wavelength of the first light receiving element and the second light receiving element are about 800 nm to about 1000 nm.

(Item 9)

The detection apparatus of any one of items 1 to 8,
wherein a distance between the first light emitting element and the first light receiving element is about 2 mm to about 3 mm, and
wherein a distance between the first light emitting element and the second light receiving element is about 4 mm to about 5 mm.

(Item 10)

An information notification system, wherein the system comprises:
the detection apparatus of any one of items 1 to 98 that obtains droplet information; and
one or more output apparatus that receives and outputs the droplet information via a network.

BRIEF DESCRIPTION OF DRAWINGS

FIG. 1 is a schematic diagram of the droplet detection apparatus of the present disclosure.

FIG. 2 is a front view of the optical element array of the present disclosure.

FIG. 3 shows an exemplary arrangement that is different from FIG. 2 of the optical element array of the present disclosure.

FIG. 4 shows the relationship between the arrangement of an optical element in the optical element array and the light receiving signal of the present disclosure.

FIG. 5 shows an exemplary droplet generation apparatus 50 that may be used together with the optical element array of the present disclosure.

FIG. 6 is a schematic diagram of the light emitting circuit and the light receiving circuit of the present disclosure.

FIG. 7 shows an exemplary method that extracts droplet information from a light receiving signal.

FIG. 8 shows a schematic diagram of the drip infusion speed notification system of the present disclosure.

DESCRIPTION OF EMBODIMENTS

The present disclosure is explained hereinafter while showing the best embodiment. Throughout the entire specification, a singular expression should be understood as encompassing the concept thereof in the plural form, unless specifically noted otherwise. Thus, singular articles (e.g., "a", "an", "the", and the like in the case of English) should also be understood as encompassing the concept thereof in the plural form, unless specifically noted otherwise. Further, the terms used herein should be understood as being used in the meaning that is commonly used in the art, unless specifically noted otherwise. Therefore, unless defined otherwise, all terminologies and scientific technical terms that are used herein have the same meaning as the general understanding of those skilled in the art to which the present disclosure pertains. In case of a contradiction, the present specification (including the definitions) takes precedence.

(Definition and the Like)

The definitions and/or basic technical contents of the terms specifically used herein are appropriately explained below.

As used herein, "droplet" refers to a mass of liquid put together with surface tension.

As used herein, "optical element array" refers to a tool wherein a plurality of optical elements are arranged on the same plane.

As used herein, "light emitting region" refers to a region wherein light irradiated from a light emitting element is irradiated on a plane comprising a pathway where a droplet passes. Furthermore, "light receiving region" refers to a region that can receive light that has directivity in a light receiving element, which is a region in a plane comprising a pathway where a droplet passes. In addition, "detection region" refers to a region where the above-mentioned "light emitting region" and "light receiving region" overlap.

As used herein, "dropping speed" refers to the amount of droplets that drop per a unit time, which may be, for example, a value expressed with a unit such as droplet number/minute, liter/time, or gram/second.

As used herein, the term "about" refers to plus or minus 10% of a shown value, unless specifically defined otherwise.

(Droplet Detection Apparatus)

In one aspect, the present disclosure provides a droplet detection apparatus. A droplet detection apparatus may comprise an optical element array having three or more optical elements comprising a first light emitting element, a first light receiving element and a second light receiving element and a reflection prevention member disposed on the opposite side of the side where the optical element array is disposed with respect to a pathway where a droplet passes. Since light reflecting to anything other than a droplet would be suppressed by providing a reflection prevention member, it is possible to improve precision of detection of dropping of a droplet in a light receiving element.

FIG. 1 shows a droplet detection apparatus 10 of an embodiment of the present disclosure. The droplet detection apparatus 10 may comprise an optical element array 11, a reflection prevention member 19, a light emitting circuit 20, a light receiving circuit 30 and a control part 40.

The optical element array may have three or more optical elements comprising a light emitting element and a light receiving element. The number of the optical elements comprised in the light emitting element array may be any number as long as the number is 3 or above. In one embodiment, the optical element array comprises four optical elements, which are two light emitting elements and two light receiving elements, but the present invention is not limited thereto. The three or more optical elements may comprise a first light emitting element, a first light receiving element and a second light receiving element, or may comprise a first light emitting element, a first light receiving element and a second light emitting element. The number of the light emitting elements and the number of the light receiving elements may be the same, or the number of the light emitting elements and the number of the light receiving elements may be different. In one embodiment, the optical element array 11 in the droplet detection apparatus 10 comprises two light emitting elements, which are a first light emitting 12 and a second light emitting element 12', and two light receiving elements, which are a first light receiving element 13 and a second light receiving element 13'. The first light emitting element 12 and the second light emitting element 12' may be any optical elements that can convert an electric signal into a light signal to send the light signal, which may be, for example, a light emitting diode (LED), organic LED, an infrared LED, an ultraviolet LED, a laser diode, or the like. The first light receiving element 13 and the second light receiving element 13' may be any optical elements that can receive a light signal to convert the light signal into an electric signal, which may be, for example, a phototransistor, a photomultiplier tube (PMT), a photodiode, an avalanche photodiode, a photoconductive cell, a photocell, or the like. In addition, the first light emitting element 12 and the second light emitting element 12' may be the same type of light emitting elements, or may be different types of light emitting elements. However, it is preferable that the first light emitting element 12 and the second light emitting element 12' are the same type of light emitting elements in order to emit the same amount of light with one light emitting circuit. The first light receiving element 13 and the second light receiving element 13' may be the same type of light receiving elements, or may be different types of light receiving elements. However, it is preferable that the first light receiving element 13 and the second light receiving element 13' are the same type of light receiving elements in order to receive the same value of light with one light receiving circuit.

Light emitted by a light emitting element and received by a light receiving element may have any wavelength to which the light emitting element and the light receiving element can adapt, preferably may have a wavelength that captures dropping of a droplet in a precise manner and is less susceptible to interference of surrounding light. In the case in which the optical element array of the present disclosure is used indoor, light used by the optical element array may have the possibility of receiving the effect of light emitted from a fluorescent lamp and receiving negative effect in the detection of a droplet. In addition, the light used by the optical element array may be desired to not be visually recognized by a human. Furthermore, the light used by the optical element array may be requested to be propagated from a light emitting element to a light receiving element via the atmosphere. Since the wavelength of a general fluorescent lamp is about 400 nm to about 700 nm, the wavelength of visible light is about 380 nm to about 780 nm, and the transmission wavelength in the atmosphere is about 300 nm to about 1000 nm, especially preferably, the light emitting wavelength of a light emitting element and the light receiving wavelength of a light receiving element may be about 800 nm to about 1000 nm.

In the optical element array of the present disclosure, optical elements may be disposed so that the light emitting region of one or more light emitting element among the three or more optical elements and the light receiving region of one or more light receiving element overlap. Preferably, a first light emitting element, a first light receiving element and a second light receiving element may be disposed within the optical element array so that a part of the light emitting region irradiated from the first light emitting element and a part of the light receiving region of the first light receiving element overlap and also a part of the light emitting region irradiated from the first light emitting element and a part of the light receiving region of the second light receiving element overlap. More preferably, the three or more optical elements further comprises a second light emitting element, wherein the first light emitting element, the first light receiving element, the second light receiving element and the second light emitting element may be disposed within the optical element array so that a part of the light emitting region irradiated from the second light emitting element and a part of the light receiving region of the first light receiving element overlap and also a part of the light emitting region irradiated from the second light emitting element and a part of the light receiving region of the second light receiving element overlap. Most preferably, the first light emitting element and the first light receiving element or the second light receiving element may be disposed on the upstream side of the pathway where a droplet passes and the second light emitting element and the second light receiving element or the first light receiving element may be disposed on the downstream side of the pathway where a dropt passes.

In the optical element array 11 of one embodiment of the present disclosure, the first light emitting element 12, the second light emitting element 12', the first light receiving element 13 and the second light receiving element 13' may be arranged on a plane 11a of the optical element array 11. FIG. 2 shows a front view of the plane 11a of the optical element array 11. The first light emitting element 12 and the second light emitting element 12' may have a first light emitting region 12a and a second light emitting region 12'a, respectively, having an area larger than the cross-sectional area of each element, and the first light receiving element 13 and the second light receiving element 13' may have a first light receiving region 13a and a second light receiving region 13'a, respectively, having an area larger that the cross-sectional area of each element. The optical element array can detect dropping of a droplet in the range where one or more light emitting region and one or more light receiving region overlap. The optical element 11 may dispose optical elements so that the light emitting region 12a of the first light emitting element 12 overlaps with the light receiving region 13a of the first light receiving element 13 and the light receiving region 13'a of the second light receiving element 13' (detection regions 15a and 15b), the light receiving region 13a of the first light receiving element 13 overlaps with the light emitting region 12a of the first light emitting element 12 and the light emitting region 12'a of the second light emitting element 12' (detection regions 15a and 15c), the light emitting region 12'a of the second light emitting element 12' overlaps with the light receiving region 13a of the first light receiving element 13 and the light receiving region 13'a of the second light receiving element 13' (detection regions 15c and 15d), and the light receiving region 13'a of the second light receiving element 13' overlaps with the light emitting region 12a of the first light emitting element 12 and the light emitting region 12'a of the second light emitting element 12' (detection regions 15b and 15d). As a result, the optical element array 11 can comprise a detection range that is wide compared to an optical element array consisting of one light emitting element and one light receiving element. Enlargement of a length 16 of a detection region in the vertical direction (hereinafter, referred to as the detection height 16) enables the time for detecting a droplet to be longer, and enlargement of a length 17 of a detection region in the horizontal direction (hereafter, referred to as the detection width 17) enables detection of dropping of a droplet even when a droplet 3 dropped while being deviated from a droplet dropping axis 4.

The optical element array 11 may determine the distance between optical elements so as to have a detection region of a sufficient droplet based on the size of a light emitting region of a light emitting element and the size of a light receiving region of a light receiving element. The distance between optical elements may be determined based on, for example, the distance to an object, amount of light of a light emitting element, light receiving sensitivity of a light receiving element, directivity of a sensor, or the like. In one embodiment, the first light emitting element 12 and the first light receiving element 13 may be arranged adjacent to one another. In other embodiments, the distance between the central position of the first optical element 12 and the central position of the first light receiving element 13 may be several tens of mm. The distance between the central position of the first light emitting element 12 and the central position of the first light receiving element 13 may be preferably about 2 mm to about 3 mm, most preferably about 2.2 mm. The distance between the central position of the first emitting element and the central position of the second light receiving element may be preferably about 4 mm to about 5 mm, most preferably about 4.9 mm.

The optical element array may be configured with a unified housing, or may be configured to consist of a plurality of housings. However, the optical element array is preferably configured to consist of a plurality of housings so as to enable arrangement of an optical element suitable for a detection subject. The optical element array 11 in the droplet detection apparatus 10 may comprise a first optical element subarray 14 comprising the first light emitting element 12 and a first light receiving element 13 and a second optical element subarray 14' comprising a second light emitting element 12' and a second light receiving element 13'. Furthermore, the optical element array 11 may be formed by the first optical element subarray 14 and the second optical element subarray 14' being arranged to be adjacent to one another. Each of the first optical element subarray 14 and the second optical element subarray 14' may be configured to be detachable from one another. Preferably, each of the first and second optical element subarrays may enable various bonds in accordance with the purpose by comprising a binding mechanism on each side. Preferably, the first optical element subarray 14 and the second optical element subarray 14' may be bound so that the light emitting elements of each thereof shown in FIG. 2 are arranged on opposite angles and the light receiving elements of each thereof are arranged on opposite angles. Furthermore, a plurality of optical element subarrays may be bound so that light emitting elements of each thereof are adjacent to one another and light receiving elements of each thereof are adjacent to one another. Furthermore, an optical element array may comprise three or more optical element subarrays.

FIG. 3 shows the arrangement of a light emitting element and a light receiving element of an optical element array based on other embodiments. FIG. 3 (*a*) is a front view of an optical element array 11' comprising a third light emitting element 12" and a third light receiving element 13" in addition to the first light emitting element 12, the first light receiving element 13, the second light emitting element 12' and the second light receiving element 13' in the optical element array 11. The optical element array 11' may have a detection width 17' greater than the detection width 17 of the optical element array 11 by comprising the third light emitting element 12" and the third light receiving element 13". Thus, the optical element array 11' can surely detect dropping of a droplet even when the droplet dropped while being greatly deviated from a droplet dropping axis.

FIG. 3(*b*) shows the front view of an optical element array 311. The optical element array 311 has an approximately triangular shape and comprises one light emitting element 312, a first light receiving element 313 and a second light receiving element 313'. The optical element array 311 may be able to detect dropping of a droplet in a portion where alight emitting region of the light emitting element 312 and a light receiving region of the first light receiving element 313 overlap and a portion where alight emitting region of the light emitting element 312 and a light receiving region of the second light receiving element 313' overlap. Thus, the optical element array 311 may have a detection height 316 and a detection width 317 that are greater compared to an optical element array consisting of one light emitting element and one light receiving element.

As discussed above, the optical element array of the present disclosure may variously arrange a light emitting element and a light receiving element within the range where a light receiving region of two or more light receiving elements overlap with a light emitting region of one light emitting element. Furthermore, the arrangement of a light emitting element and a light receiving element may be determined based on, for example, the signal measurement speed of a light receiving signal, droplet dropping speed, the size of discrepancy of a droplet deviating from a droplet dropping axis and the like. FIG. 4 is a graph showing the relationship between light receiving signal intensity and time. FIG. 4(*a*) and FIG. 4(*b*) are light receiving signal data regarding the same light receiving signal 45. In this embodiment, a controlling part 40 may detect dropping of a droplet by extracting a light receiving signal that exceeds a threshold value 48 as discussed below. When the measurement speed of a light receiving signal is sufficiently high like in FIG. 4 (*a*), the control part 40 may detect a plurality of high light receiving signals of when a droplet dropped and detect dropping of the droplet. Meanwhile, when the measurement speed of a light receiving signal in a conventional droplet detection apparatus is low (or when the detection region is small) like in FIG. 4(*b*), a light receiving signal that exceeds the threshold value 48 cannot be detected and dropping of a droplet may be failed to be detected. In such a case, an optical element array 11 with great detection height 16 (wide detection range) may be used. The optical element array 11 may detect dropping of a droplet for a longtime and surely detect a light receiving signal that exceeds the threshold value 48 compared to the case of using an optical element array with a small detection height 16.

Furthermore, the arrangement of alight emitting element and a light receiving element in an optical element array may also depend on the configuration of an apparatus that generates a droplet. For example, when the detection region of an optical element array is large, a droplet that has not dropped may be detected. In this regard, in view of FIG. 5, FIG. 5 shows an exemplary droplet generation apparatus 50. The droplet generation apparatus 50 has a droplet tube 51 and a droplet generation part 52, wherein a droplet dropped from the droplet generation part 52 passes within the droplet tube 51 and accumulates at a lower part of the droplet tube 51. When the droplet detection apparatus of the present disclosure detects a droplet 3*a* being generated that still has not dropped, the dropping speed may not be able to be accurately calculated. In addition, when the detection region of the droplet detection apparatus reaches a liquid pool 3*c*, there is a possibility of the droplet detection apparatus detecting a ripple occurred in a liquid pool due to dropping of a droplet, a splash of a droplet and the like as a droplet. Thus, the optical element array 11 may be configured to have a detection height 516 that does not comprise a droplet 3*a* being generated and a liquid pool 3*c* so that the droplet detection apparatus of the present disclosure can detect only a droplet 3*b* that is dropping without detecting a droplet 3*a* being generated, a ripple in a liquid pool 3*c* and the like. For example, when the length from the tip of the droplet generation part 52 to the surface of the liquid pool 3*c* is 38 mm, the detection height 516 of the optical element array may be 34 mm.

As discussed above, the arrangement of a light emitting element and a light receiving element in an optical element array may be determined based on the droplet dropping speed, signal measurement speed, configuration of the apparatus that generates the droplet, size of the discrepancy of a droplet deviating from a droplet dropping axis and the like. For example, an appropriate detection region may be able to be set by an optical element array comprising a plurality of optical element subarrays as discussed above.

In this regard, in view of FIG. 1 again, the plane 11*a* of the optical element array 11 may be directed to the droplet dropping axis 4. The droplet dropping axis 4 may be any axis along a pathway where the droplet 3 drops, which may be, for example, a straight axis extending in the approximately vertical direction in which the droplet 3 drops in accordance with gravity. The upper side on the paper surface of FIG. 1 is the upstream side of the droplet and the lower side shows the downstream side.

The reflection prevention member 19 may be any member that prevents reflection of light, which may be a member comprising an approximate plane so as to evenly absorb light. The reflection prevention member 19 may be formed with any material, which may be configured with, for example, resin. The reflection prevention member 19 may preferably be formed with a black color material so as to be able to absorb light. The reflection prevention member 19 may be disposed opposite to the plane 11*a* of the optical element array 11 while sandwiching the droplet dropping axis 4. The reflection prevention member 19 may preferably be disposed in parallel with the plane 11*a* of the optical element array 11 so as to evenly absorb light sent from the first light emitting element 12 and the second light emitting element 12' of the optical element array 11. In addition, in another embodiment, the reflection prevention member 19 may have an uneven surface or a curved surface so as to let the light sent from the first light emitting element 12 and the second light emitting element 12' escape outside the light receiving region of the first light receiving element 13 and the second light receiving element 13'.

A light emitting element of a light element array is connected to a light emitting circuit and a light receiving element is connected to a light receiving circuit. In the droplet detection apparatus 10, the first light emitting element 12 and the second light emitting element 12' may be connected to a light emitting circuit 20 and the first light receiving element 13 and the second light receiving element 13' may be connected to a light receiving circuit 30. The light emitting circuit 20 may comprise any circuit element that generates an electric signal that is suitable for the intensity of light irradiated to the first light emitting element 12 and the second light emitting element 12', and the light receiving circuit 30 may comprise any circuit element that transmits an electric signal, which had been received and converted by the first light receiving element 13 and the second light receiving element 13', to the control part 40.

FIG. 6 shows an exemplary configuration of a circuit of a droplet detection apparatus. The configuration of the circuit shown in FIG. 6 is just an example and the configuration is not limited thereto.

The circuit comprises a light emitting circuit 20 and a light receiving circuit 30. The light emitting circuit 20 may comprise a power source 21, a resistor 22 for regulating the amount of emitted light, a resistor 23 for preventing eddy current and a ground 31. The power source 21 may be any power source that generates an electric signal sent to a light emitting element, which may include, for example, a fixed power source and a variable power source. The power source 21 may be directly corrected to the first light emitting element 12 and a second light emitting element 12', or may be connected via other elements.

An electric signal dispatched from the power source 21 may reach the resistor 22 for regulating the amount of emitted light. The resistor 22 for regulating the amount of emitted light may be any variable resistor that may regulate the intensity of an electric signal dispatched from a power source.

An electronic signal that passed the resistor 22 for regulating the amount of emitted light may reach the resistor 23 for preventing eddy current. The resistor 23 for preventing eddy current may be any resistor that can remove eddy current within the light emitting circuit 20.

An electric signal that passed the resistor 23 for preventing eddy current may be sent to the first light emitting element 12 and the second light emitting element 12'. The first light emitting element 12 and the second light emitting element 12' may convert a received electric signal into a light signal to dispatch the light signal. Furthermore, the first light emitting element 12 and the second light emitting element 12' may be connected to a ground 31.

The light receiving circuit 30 may comprise a power source 21, a ground 31 and a resistor 32 for regulating sensitivity to received light. An electric signal dispatched from the power source 21 may reach the first light receiving element 13 and the second light receiving element 13'. The first light receiving element 13 and the second light receiving element 13' may receive a light signal reflected by a droplet and convert the received light signal into an electric signal to output to the control part 40.

In addition, the electric signal outputted by the first light receiving element 13 and the second light receiving element 13' may be regulated regarding sensitivity to received light with the resistor 32 for regulating sensitivity to received light. In the droplet detection apparatus 10, the intensity of an electric signal when a droplet is not detected is desirably 0, but actually the effect of ambient light is received and some intensity of an electric signal may be outputted. The resistor 32 for regulating sensitivity to received light may be any variable resistor that removes or minimizes the effect of such ambient light to detection of a droplet. For example, the resistor 32 for regulating sensitivity to received light may regulate the size of an electric signal outputted to the control part 40 while considering the size of an output signal that detects a droplet and the size of an output signal due to ambient light. The resistor 32 for regulating sensitivity to received light may be connected to the ground 31.

An electric signal outputted to the control part 40 may be a signal having any parameter, which may be, for example, a voltage or a current. However, it is preferable to output an electric signal as a voltage for easiness of measurement. In such a case, the voltage applied to the resistor may be outputted to the control part 40 as an electric signal as a current by adding the resistor to output of a light receiving element.

The control part 40 may determine the amount of emitted light of the first light emitting element 12 and the second light emitting element 12' and detect dropping of a droplet from the amount of received light of the first light receiving element 13 and the second light receiving element 13'. The control part 40 may be any control apparatus, which may be, for example, a processor, a microprocessor, an integrated circuit, a microcontroller, or the like.

The control part 40 may detect dropping of a droplet by extracting droplet dropping information from a light receiving signal regarding a droplet that passed a detection region and dropped. The method of extracting droplet dropping information by the control part 40 may be any method, which preferably may carry out A/D conversion of a light receiving signal for clear identification between when a droplet dropped and when a droplet has not dropped. FIG. 7 shows an exemplary method of carrying out A/D conversion of a light receiving signal and extracting droplet dropping information.

FIG. 7(*a*) shows raw data of a light receiving signal received by the control part 40. The raw data of the light receiving signal may be any data, which may be, for example, analog data such as successive electric signals. In this example, the light receiving signal intensity would be maximum in time point $t_1$ and time point $t_2$. Regarding the raw data of the light receiving signal, a threshold value 38 may be set. The threshold value 38 may be any value that can determine when a droplet is passing a detection region and when a droplet is not passing the detection region. However, the threshold value 38 is preferably a value sufficiently low compared to the light receiving signal intensity of when a droplet is passing a detection region and a value sufficiently high compared to the light receiving signal intensity of when a droplet is not passing a detection region.

FIG. 7(*b*) shows data wherein the raw data of a light receiving signal is digitalized. Digital data of a light receiving signal may set the value exceeding the threshold value 38 as 1 and set the value that is not exceeding the threshold value 38 as 0. The threshold value 38 may be any value that can distinguish between the signal intensity when a droplet is passing and the signal intensity when a droplet is not passing.

FIG. 7(*c*) shows data of integration of values of digital data of a light receiving signal in order to temporarily identify the dropping time pint of a droplet from the digital data of the light receiving signal. The integrated value may be a value of integration of values of the digital data of the light receiving signal. When the digital value is 1, the integrated data would elevate to 1, and while the digital value continues to be 1, the integrated value would keep elevating. Furthermore, when the digital value drops from 1 to 0, the integrated value would be consistent. Furthermore, when the integrated value continues to be the same value, the integrated value may be reset.

FIG. 7(*d*) shows droplet detection data that had been binarized to take out drop droplet information from integrated data. The droplet detection data may be any data that can identify dropping of a droplet with a constant criterion. In the case of using binarized data to take out droplet information, a detection value 48' may be determined. In this embodiment, the detection value 48' may be integrated value 1 in the integrated data of FIG. 7(*c*). Furthermore, binarization, wherein a value matching the detection value 48' is set as 1 and a value not matching the detection value 48' is set as 0, is carried out to temporarily determine the dropping time point of one droplet, which enables the time between the droplet dropping time points to be derived as the dropping speed.

Information obtained from droplet detection data may undergo processing by the control part 40 as droplet dropping information. For example, the control part 40 may send the droplet dropping information to other devices and/or networks and/or use the droplet dropping information to perform further processing. The droplet dropping information may be any information quantitatively showing dropping of a droplet, which may be, for example, droplet dropping time point, or droplet dropping speed (e.g., drop count/minute, drop count/hour, liter/minute, liter/hour, gram/minute, or gram/time, or the like). In this method, the time point when the integrated value is 1 in the integrated data of FIG. 7(*c*) may be calculated as the droplet dropping time point. Furthermore, the droplet dropping speed (e.g., drop/minute) may be derived from successive droplet dropping time points.

The method of extracting droplet dropping information shown in FIG. 7 is exemplary, and dropping of a droplet may be detected by other methods. While the example of FIG. 7 converts digitalized light receiving signal data into integrated data and further carries out binarization to detect dropping of a droplet, the droplet information may be extracted without going through integration by, for example, determining that the time point when the value turned from 0 to 1 in the digital data of the light receiving signal as the droplet dropping time point.

(Information Notification System)

In one aspect, the present disclosure provides an information notification system that notifies a user the information regarding dropping of a droplet. The information notification system of the present disclosure may comprise a detection apparatus that obtains droplet information, a network where the droplet information is communicated and one or more output apparatus that receives and outputs droplet information. FIG. 8 shows a drip infusion speed notification system 80 that notifies a physician and/or nurse the dropping speed of drip infusion of a patient in a medical institution. The information notification system of the present disclosure is not limited thereto and may be, for example, a water-feeding speed notification system used to feed water to a plant.

The drip infusion speed notification system 80 may comprise a detection apparatus 81, a network 82, a server 83, one or more router 84 and one or more user terminal 85. The detection apparatus 81 may be any apparatus that can detect drip infusion speed, which may be, for example, the droplet detection apparatus 10 discussed above. The detection apparatus 81 may be connected to the network 82 so as to be able to notify the detected drip infusion speed information to the server 83 and/or the one or more user terminal 85.

The network 82 may be any network that can be utilized among a plurality of terminals, which may be, for example, LAN, WAN, or the like. In this medical institution, various devices are connected to the network 82 and various information may be sent/received via the network 82.

One or more router 84 may be provided within the medical institution to connect various devices to the network 82.

The server 83 may receive drip infusion speed information via the network 82, store the received drip infusion speed information and send the drip infusion speed information to the one or more user terminal 85. In this embodiment, the drip infusion speed notification system 80 is shown to have one server, but is not limited thereto and may have a plurality of servers.

The one or more user terminal 85 may obtain drip infusion speed information from the server 83. The one or more user terminal 85 may be any terminal that can be owned by any user such as a physician and/or nurse, which may be, for example, a smart phone, a mobile phone, a tablet, a smart watch, or the like. Drip infusion speed information may be sent to the one or more user terminal 85 in any format, and, for example, may be sent via email, or may be sent as a message in a dedicated application. Preferably, drip infusion speed information may be sent as a message within a dedicated application so that the one or more user terminal 85 always obtains the latest drip infusion speed information. A user that owns the one or more terminal 85 can remotely confirm whether or not drip infusion of a patient is appropriately performed by confirming the sent drip infusion speed information.

The one or more user terminal 85 is one example of the output apparatus in the information notification system of the present disclosure, and may comprise other devices. For example, the output apparatus may be a display lamp, a speaker, or the like, and may be provided at a location where a medical worker is waiting (e.g., a nurses' station or the like).

In the drip infusion speed notification system 80 shown in FIG. 8, the one or more router 84 comprises four routers 84a, 84b, 84c and 84d. The four routers 84a, 84b, 84c and 84d are disposed at different locations. In addition, in the drip infusion speed notification system 80, the one or more user terminal 85 comprises three user terminals 85a, 85b and 85c, wherein the three user terminals 85a, 85b and 85c are owned by different users.

The routers 84a, 84b, 84c and 84d connect the detection apparatus 81 and user terminals 85a, 85b and 85c to the network 82. The detection apparatus 81 and user terminals 85a, 85b and 85c are set to connect to a router that is most closely disposed. In the example shown in FIG. 8, the user terminal 85a is connected to the router 84a, the user terminal 85b is connected to the router 84b, the user terminal 85c is connected to the router 84c and the detection apparatus 81 is connected to the router 84d. This enables the user terminals 85a, 85b and 85c to always maintain the state of being connected to the network 82, wherein it is possible to notify drip infusion speed information of a patient via a network.

When there is abnormality in the drip infusion speed information sent by the detection apparatus 81 to the server 83 via the network 82, the server 83 may notify a user terminal a drip infusion abnormality warning. The drip infusion abnormality warning may be sent from the server 83 to the network 82. The network 82 may determine whether or not there is a user terminal connected to the router 84d to which the detection apparatus 81 is connected among the routers 84a, 84b, 84c and 84d. When there is a user terminal connected to the router 84d, the drip infusion abnormality warning may be sent to said user terminal. Meanwhile, when there is no user terminal connected to the router 84d, the network 82 may notify the drip infusion abnormality warning to the user terminal 85c connected to the router 84c that is most closely disposed to the router 84d. If there is also no user terminal connected to the router 84c, the router 84b and the router 84a may be further searched in order. As such, a user who owns a user terminal can quickly go to a patient and take appropriate measures by notifying drip infusion abnormality warning to a user terminal that is present near the detection apparatus 81 based on router position information.

The drip infusion speed notification system 80 explained above in view of FIG. 8 is merely an example of the information notification system of the present disclosure, and other systems which are partially different from the configuration of the drip infusion notification system 80 may also be encompassed by the scope of the information notification system of the present disclosure. For example, a different system configuration may be employed depending on the scale of the medical institution. For example, in a clinic managed by an individual where it is difficult to provide a dedicated server and does not have a wide space, droplet information of a user obtained from a detection apparatus may be sent to a cloud, managed on the cloud and directly sent from the cloud to a user terminal without utilizing a router and a server. In addition, in a small-scale hospital that has a dedicated server but not a wide space, other output apparatuses such as a display lamp, a speaker, or the like may be used instead of a user terminal and drip abnormality warning may be notified to a medical worker through the output apparatus by providing the output apparatus to a nurses' station or the like. Furthermore, in a mid-scale hospital and large-scale hospital that have a dedicated server and large space, the above-mentioned drip infusion speed notification system 80 may be used since there is a need to notify a warning to a medical worker near a patient whose drip infusion abnormality warning has been issued.

The present disclosure enables obtainment of a detection apparatus with improved ability to detect dropping of a droplet. The detection apparatus of the present disclosure can efficiently have a wide detection region since there are a plurality of light receiving regions of a light receiving element that overlap with the light emitting region of one light emitting element compared to a conventional detection apparatus which has a light receiving region of one light receiving element overlapping with a light emitting region of one light emitting element. As a result, it is possible to detect a droplet in a wide range without expanding the detection region using a lens or the like.

In addition, the information notification system of the present disclosure enables confirmation of droplet information by a remote user, wherein a user such as a medical worker can take prompt measures when there is abnormality in dropping of a droplet.

While the present invention has been exemplified using preferable embodiments of the present invention as described above, the present invention should not be limited to the above-discussed embodiment. It is understood that the scope of the present invention should be interpreted only by the Claims. It is understood that those skilled in the art can perform an equivalent scope based on the specific description of the preferable embodiment of the invention of the present disclosure and common general knowledge. Any document cited herein should be incorporated herein by reference in the same manner as the contents are specifically described herein.

INDUSTRIAL APPLICABILITY

The present disclosure is useful for providing a detection apparatus with improved ability to detect dropping of a droplet.

REFERENCE SIGNS LIST

3 Droplet
4 Droplet dropping axis
10 Droplet detection apparatus
11 Optical element array
11a Surface
12 First light emitting element
12' Second light emitting element
12a Light emitting region of a first light emitting element
12'a Light emitting region of a second light emitting element
13 First light receiving element
13' Second light receiving element
13a Light receiving region of a first light receiving element
13'a Light receiving region of a second light receiving element
14 First optical element subarray
14' Second optical element subarray
15a, 15b, 15c, 15d Detection region
16 Detection height
17 Detection width
19 Reflection prevention member
20 Light emitting circuit
30 Light receiving circuit
40 Control part

The invention claimed is:

1. A detection apparatus that detects dropping of a droplet, wherein the detection apparatus comprises:
an optical element array having four or more optical elements comprising a first light emitting element, a first light receiving element, a second light emitting element and a second light receiving element,
wherein the first light emitting element, the first light receiving element and the second light receiving element are disposed within the optical element array so that:
a part of a light emitting region irradiated from the first light emitting element and a part of a light receiving region of the first light receiving element overlap; and
a part of a light emitting region irradiated from the first light emitting element and a part of a light receiving region of the second light receiving element overlap,
wherein the first light emitting element, the first light receiving element, the second light receiving element and the second light emitting element are disposed within the optical element array so that:
a part of a light emitting region irradiated from the second light emitting element and a part of a light receiving region of the first light receiving element overlap; and
a part of a light emitting region irradiated from the second light emitting element and a part of a light receiving region of the second light receiving element overlap,
wherein the second light emitting element and the first light receiving element are disposed on an upstream side of a pathway where the droplet passes, and
wherein the second light emitting element and the first light receiving element are disposed on a downstream side of pathway where the droplet passes.

2. The detection apparatus of claim 1, wherein the optical element array comprises:
a first optical element subarray comprising a first light emitting element and a first light receiving element; and
a second optical element subarray comprising a second light emitting element and a second light receiving element,
wherein the first optical element array and the second optical element array are disposed adjacent to one another.

3. The detection apparatus of claim 2, wherein the second optical element subarray is configured to be detachable with respect to the first optical element subarray.

4. The detection apparatus of claim 1, comprising a reflection prevention member disposed on the other side of a side where the optical element array is disposed with respect to a pathway where the droplet passes.

5. The detection apparatus of claim 4, wherein the reflection prevention member comprises a black color region.

6. The detection apparatus of claim 1, wherein a light emitting wavelength of the first light emitting element and a light receiving wavelength of the first light receiving element and the second light receiving element are about 800 nm to about 1000 nm.

7. The detection apparatus of claim 1,
wherein a distance between the first light emitting element and the first light receiving element is about 2 mm to about 3 mm, and
wherein a distance between the first light emitting element and the second light receiving element is about 4 mm to about 5 mm.

8. An information notification system, wherein the system comprises:
the detection apparatus of claim 1 that obtains droplet information; and
one or more output apparatus that receives and outputs the droplet information via a network.

* * * * *